(12) United States Patent
Schwartz et al.

(10) Patent No.: US 6,371,942 B1
(45) Date of Patent: *Apr. 16, 2002

(54) AUTOMATIC MANIFOLD FOR VASCULAR CATHETER

(75) Inventors: Robert S. Schwartz; David R. Holmes; David Berry, all of Rochester, MN (US); Donald G. Ellis, Boulder, CO (US)

(73) Assignee: Mayo Foundation for Medical Education and Research, Rochester, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/159,008

(22) Filed: Sep. 23, 1998

(51) Int. Cl.[7] ............................................. A61M 5/00
(52) U.S. Cl. .................... 604/246; 604/247; 604/258; 604/83; 137/606; 137/896; 251/149
(58) Field of Search ................ 251/149; 137/614.2, 137/322, 602, 606, 896; 604/246, 247, 83, 118, 258

(56) References Cited

U.S. PATENT DOCUMENTS

| | | |
|---|---|---|
| 4,246,932 A | 1/1981 | Raines |
| 4,310,017 A | 1/1982 | Raines |
| 4,535,820 A | 8/1985 | Raines |
| 4,556,086 A | 12/1985 | Raines |
| 4,608,996 A * | 9/1986 | Brown ........................ 128/760 |
| 4,729,401 A | 3/1988 | Raines |
| 4,804,358 A * | 2/1989 | Karcher et al. ............... 600/17 |
| 4,915,688 A * | 4/1990 | Bischof et al. ............... 604/83 |
| 5,037,390 A | 8/1991 | Raines et al. |
| 5,064,168 A | 11/1991 | Raines et al. |
| 5,127,904 A * | 7/1992 | Loo et al. ..................... 604/83 |
| 5,328,463 A | 7/1994 | Barton et al. |
| 5,356,375 A * | 10/1994 | Higley ........................ 604/30 |
| 5,378,229 A | 1/1995 | Layer et al. |
| 5,688,244 A | 11/1997 | Lang |

FOREIGN PATENT DOCUMENTS

| DE | 196 43 360 C 1 | 5/1998 |
|---|---|---|
| WO | WO 96/24791 | 8/1996 |

OTHER PUBLICATIONS

B. Braun Medical Inc. Brochure, 1 page (1995).

* cited by examiner

Primary Examiner—Richard K. Seidel
Assistant Examiner—Jeremy Thissell
(74) Attorney, Agent, or Firm—Merchant & Gould P.C.

(57) ABSTRACT

An automatic manifold for a catheter assembly. Valve means automatically open and close flow between a liquid supply port for connection to injection means and a liquid delivery port for communication with the catheter assembly. A pressure sensor is integrated into the manifold. The manifold also includes a quick-disconnect coupling mechanism for a liquid supply port.

16 Claims, 1 Drawing Sheet

AUTOMATIC MANIFOLD FOR VASCULAR CATHETER

FIELD OF THE INVENTION

This invention relates generally to devices used with vascular catheters, and more particularly to manifolds for delivering liquids to the patient through the catheter.

BACKGROUND OF THE INVENTION

Manifolds for delivering liquids, such as contrast media, saline and drugs, through a catheter are known in the art. The manifold has a number of ports through which different liquids are supplied and an outlet port through which liquid is delivered. A device, such as a power injector or syringe, connected to another port, draws liquid from a selected supply port and then forces the liquid into the catheter via the delivery port. The manifold thus acts as a traffic-keeping device of sorts which is manipulated by the operator to deliver different liquids to the patient as needed.

One of the problems associated with the manifolds in use today is that the valves employed to direct liquids are fully manual. For example, the MORSE® MANIFOLD most commonly used employs manual stopcock valves to control flow from the various liquid supply ports, to and from the injector, and to the liquid delivery port. Each time it is desired to deliver a particular liquid to a patient, one or more of these stopcocks first must be manually moved to draw liquid into the injector, and then again must be manually moved to inject the liquid into the catheter. This wastes time, which is particularly valuable when performing diagnostic, therapeutic or interventional vascular procedures, is a distraction during such procedures, and requires the use of an extra hand. There is also the possibility that the stopcocks could accidentally be moved to the wrong positions such that the wrong fluid is delivered, an air bubble is created, or some other risk to the patient occurs. These risks are of particular concern as nonphysicians become more involved with procedures.

What has been needed is a manifold for a catheter assembly which automatically controls flow between the liquid supply ports and the liquid delivery port when injecting liquid into the patient.

SUMMARY OF THE INVENTION

According to the present invention, an automatic manifold for a catheter assembly is provided. The automatic manifold could be employed in a variety of venous medical device assemblies, including cardiac, neurological and arterial applications.

In one aspect of the invention, the automatic manifold comprises a housing having a liquid delivery port for communication with the catheter assembly, and a liquid supply port for connection to an injector. A chamber defined in the housing is in fluid communication with the liquid delivery and supply ports. A one-way valve controls flow between the supply and delivery ports and through the chamber. The valve is biased toward a closed position and is constructed and arranged to move to an open position when liquid is forced into the supply port under pressure.

In another aspect of the invention, the automatic manifold comprises a liquid delivery port for communication with a catheter assembly, and a liquid supply port for connection to an injector. A valve mechanism automatically opens flow between the supply and delivery ports when liquid is forced into the supply port under pressure, and automatically closes flow between the supply and delivery ports when liquid no longer is forced into the supply port.

These and other advantages and features of novelty which characterize the invention are pointed out with particularity in the claims annexed hereto. However, for a better understanding of the invention and its advantages, reference should be made to the drawing which forms a further part hereof, and to the accompanying descriptive matter in which there is illustrated and described a preferred embodiment of the invention.

DETAILED DESCRIPTION OF THE PREFERRED EMBODIMENT

Figure 1:
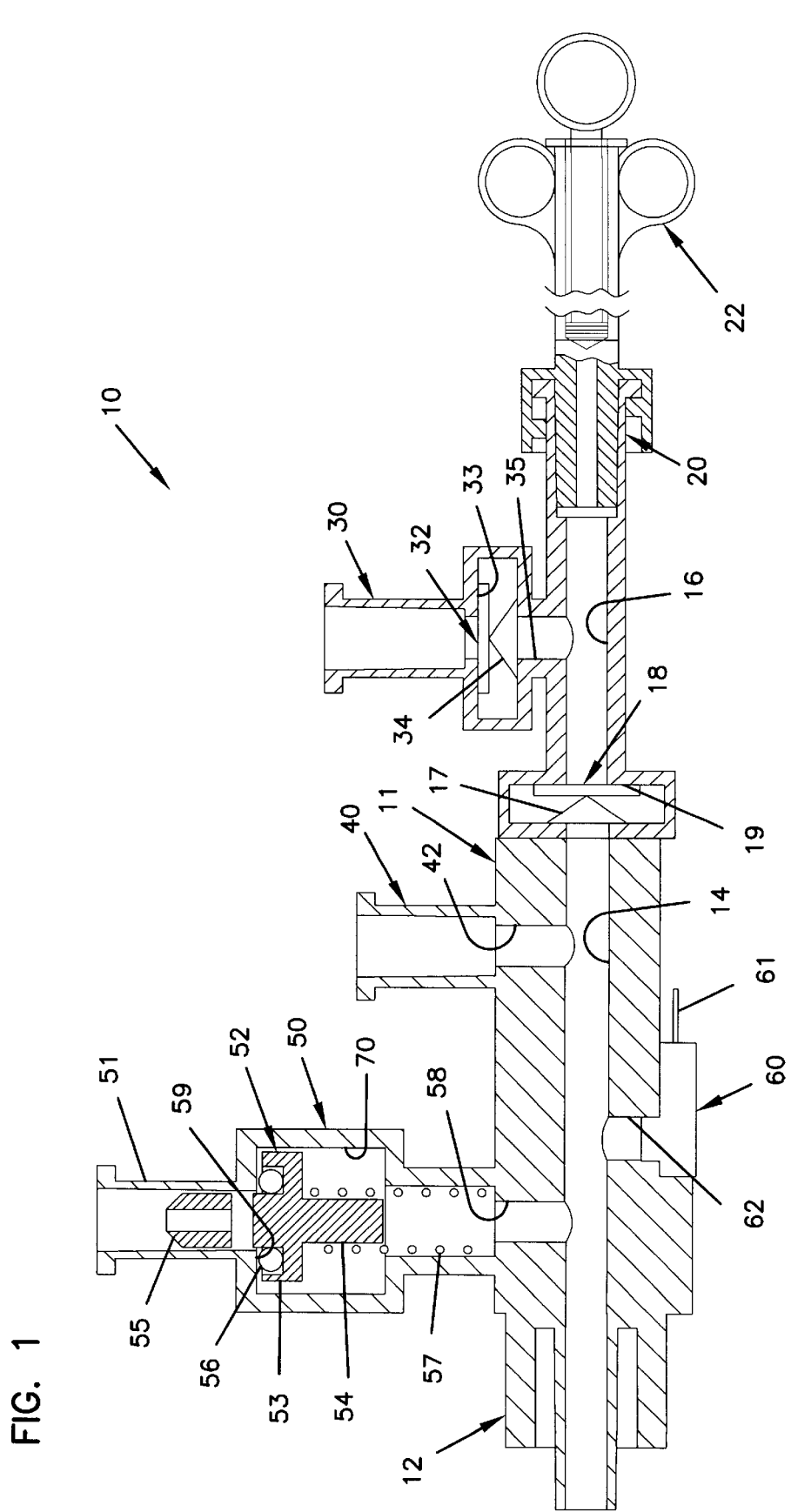
FIG. 1 is a cross-sectional view of an automatic manifold according to the present invention.

Referring now to the drawings, an embodiment of the automatic manifold of the present invention is shown in FIG. 1.

Manifold 10 comprises housing 11 including liquid supply 20 and delivery 12 ports connected by first 14 and second 16 chambers. Check valve 18 between chambers 14, 16 controls flow between supply 20 and delivery 12 ports. Valve 18 is a one-way valve known (see U.S. Pat. No. 4,535,820) and available (from Burron Medical Inc. of Bethlehem, Pennsylvania) for medical applications. Valve 18 is made of elastomeric material supported by conical member 17 against seating surface 19 to a closed position (shown). When liquid is forced under pressure into supply port 20 by syringe 22, valve 18 automatically opens (by lifting from surface 19) to allow the liquid to pass into chamber 14, out delivery port 12 and into the catheter (not shown). After liquid is no longer being forced through valve 18 by syringe 22, valve 18 automatically closes (against surface 19) so as to isolate supply port 20 (and second chamber) from first chamber 14.

First liquid supply port 30 communicates with second chamber 16 via passage 35, flow being controlled by another one-way valve 32 including a conical member 34 and seating surface 33. When syringe 22 draws liquid from second chamber 16, valve 18 automatically stays closed and valve 32 automatically opens so that liquid is drawn into first supply port 30, through second chamber, and into syringe 22. When syringe 22 is depressed, valve 32 automatically stays closed and valve 18 automatically opens as discussed above.

Employing one or more automatic one-way valves in this way permits supplying liquids to the patient without having to manually manipulate various valves. The necessary opening and closing between ports, chambers and/or passages is automatically done simply by operating an injector to draw in and then force out liquid.

It will be understood that the makeup of, and arrangement of, the various components could be varied to achieve similar results. For example, first supply port 30 (or additional supply ports) need not necessarily have a one-way valve, but could use a manual or another valve control means. A power injector, or other pressure-generating device, could be employed instead of a syringe. Various automatic one-way valve designs could be employed.

In the preferred embodiment, there are four liquid supply ports 20, 30, 40, 50 (not including the syringe port 20), only one (30) of which has a one-way valve 32. The latter three (30, 40, 50) act as inlets for different liquids, specifically contrast media, saline, and drugs, respectively, in the preferred embodiment. It will be understood that these ports could be rearranged, some taken away, or others added, within the principles of the invention. Further one-way valves associated with particular ports, in various arrangements, could also be employed.

Second supply port 40 communicates with first chamber 14 via passage 42. This port is intended for saline flushing liquid, such as a slow continuous flush, a fast periodic flush, or both.

Third supply port 50 is intended for drug delivery and includes a novel coupling mechanism 52. When a standard threaded male Luer (such as 12, threads not shown) is threaded onto female Luer 51, the central protrusion of the male Luer (see 12 again) abuts against head 55 and compresses spring 57 on stem 54 of plunger 53, thereby moving O-ring 56 away from seat 59. Liquid then flows into and around head 55 and around the rest of plunger 53, through chamber 70 and passage 58, and into first chamber 14. When the male Luer is unthreaded, spring 57 automatically returns coupling mechanism 52 to a closed position (shown). In this way, a reliable and simple seal is created where, as when introducing drugs, it is desired to have the capability to quickly connect different liquid sources to, and disconnect them from, the manifold. It will be understood that the components of coupling 52, and their arrangement, could be varied within the principles of the invention.

When liquid is injected into either second 40 or third 50 supply ports, valve 18 automatically stays closed.

Manifolds known today are connected to a pressure sensor/monitor via another port and a line communicating liquid from the manifold to the sensor/monitor. This is undesirable because readings can sometimes be inaccurate (due to the liquid in the line limiting frequency response, or due to a bubble in the line) and the additional line can be cumbersome. The novel design herein accordingly incorporates a pressure sensor 60 directly into the manifold. Sensor 60 employs a pressure transducer (such as the Motorola MPX2300D) which senses pressure directly from chamber 14 and transmits an electronic signal to a monitor (not shown) via electrical leads 61.

It will be understood that the last three components discussed (40, 50, 60) could be arranged in different locations. For example, 40 or 50 could be located on an upstream side of valve 18 in communication with second chamber 16. Various other arrangements could also be imagined.

It should be understood that the present invention is not limited to the preferred embodiment discussed above, which is illustrative only. Changes may be made in detail, especially in matters of the type, arrangement, shape and size of components within the principles of the invention, to the full extent indicated by the broad general meanings of the terms in which the appended claims are expressed.

We claim:

1. A manifold for delivering liquids to a patient, comprising:
   (a) a housing having a liquid delivery port for communication with the patient and an injection port for connection to an injector;
   (b) first and second chambers defined in said housing in fluid communication with said liquid delivery and injection ports;
   (c) a first one-way valve between said chambers, biased toward a closed position, and constructed and arranged to move to an open position when liquid is forced from said second to said first chamber;
   (d) a first liquid supply port, communicating with said second chamber, and having a second one-way valve that is biased toward a closed position and is constructed and arranged to move to an open position when liquid is drawn through said first supply port and into said second chamber;
   (e) a second liquid supply port communicating with said first chamber;
   (f) wherein when liquid is drawn into said first liquid supply port by the injector, said first and second valves are automatically closed and opened respectively, and when liquid is forced out said liquid delivery port by the injector, said first and second valves are automatically opened and closed respectively; and
   (g) a third supply port having a coupling mechanism wherein said coupling mechanism includes a male Luer and a female Luer, and said male and female Luers taken together perform a plunger movement allowing liquid flow into said first chamber.

2. A manifold according to claim 1, wherein said first liquid supply port is constructed and arranged for receiving contrast media.

3. A manifold according to claim 1, wherein said second liquid supply port is constructed and arranged for receiving saline.

4. A manifold according to claim 1, further including a third liquid supply port, communicating with said first chamber, and constructed and arranged for receiving drugs.

5. A manifold according to claim 1, wherein said injection port is constructed and arranged for connection to a power injector.

6. A manifold according to claim 1, wherein said injection port is constructed and arranged for connection to a syringe.

7. A manifold according to claim 1, further including a pressure port connecting said first chamber to a pressure monitor.

8. A manifold according to claim 7, wherein said pressure monitor comprises a pressure sensor integrated as part of the manifold.

9. A manifold according to claim 1, wherein said one-way valves comprise an elastomeric material.

10. A manifold for a catheter assembly, comprising:
    (a) a housing having a liquid delivery port for communication with the catheter assembly and an injection port for connection to an injector;
    (b) a chamber defined in said housing in fluid communication with said liquid delivery and injection ports;
    (c) a first liquid supply port in fluid communication with said chamber, constructed and arranged for receiving saline;
    (d) a second liquid supply port in fluid communication with said chamber, constructed and arranged for receiving contrast media; and
    (e) a third supply port having a coupling mechanism wherein said coupling mechanism includes a male Luer and a female Luer, and said male and female Luers taken together perform a plunger movement allowing liquid flow into said chamber.

11. A manifold for a catheter assembly according to claim 10, wherein a blood pressure sensor is integrated as a part of the manifold, said sensor communicating with said first chamber.

12. A manifold for delivering liquids to a patient, comprising:
    (a) a housing having a liquid delivery port for communication with the patient and an injection port for connection to an injector;

(b) first and second chambers defined in said housing in fluid communication with said liquid delivery and injection ports;

(c) a first one-way valve between said chambers, biased toward a closed position, and constructed and arranged to move to an open position when liquid is forced from said second to said first chamber;

(d) a first liquid supply port, communicating with said second chamber, and having a second one-way valve that is biased toward a closed position and is constructed and arranged to move to an open position when liquid is drawn through said first supply port and into said second chamber;

(e) a second liquid supply port communicating with said first chamber;

(f) wherein when liquid is drawn into said first liquid supply port by the injector, said first and second valves are automatically closed and opened respectively, and when liquid is forced out said liquid delivery port by the injector, said first and second valves are automatically opened and closed respectively; and (g) wherein the first and second chambers are aligned to each other along a longitudinal axis of the manifold and the first and second liquid supply ports communicate with the second and first chambers along a transversal axis of the manifold, respectively.

13. A manifold for delivering liquids to a patient according to claim 12, wherein a third supply port having a coupling mechanism wherein said coupling mechanism includes a male Luer and a female Luer, and said male and female Luers taken together perform a plunger movement allowing liquid flow into said first chamber.

14. A manifold for a catheter assembly, comprising:

(a) a housing having a liquid delivery port for communication with the catheter assembly and an injection port for connection to an injector;

(b) first and second chambers defined in said housing in fluid communication with said liquid delivery and injection ports;

(c) a first liquid supply port in fluid communication with said second chamber, constructed and arranged for receiving saline;

(d) a second liquid supply port in fluid communication with said first chamber, constructed and arranged for receiving contrast media; and (e) wherein the first and second chambers are aligned to each other along a longitudinal axis of the manifold and the first and second liquid supply ports communicate with the second and first chambers along a transversal axis of the manifold, respectively.

15. A manifold for a catheter assembly according to claim 14, wherein a third supply port having a coupling mechanism wherein said coupling mechanism includes a male Luer and a female Luer, and said male and female Luers taken together perform a plunger movement allowing liquid flow into said first chamber.

16. A manifold for a catheter assembly according to claim 14, wherein a blood pressure sensor is integrated as a part of the manifold, said sensor communicating with said first chamber.

\* \* \* \* \*

UNITED STATES PATENT AND TRADEMARK OFFICE
CERTIFICATE OF CORRECTION

PATENT NO.     : 6,371,942 B1
DATED          : April 16, 2002
INVENTOR(S)    : Schwartz et al.

It is certified that error appears in the above-identified patent and that said Letters Patent is hereby corrected as shown below:

<u>Title page,</u>
Item [75], city name "Boulder" should read -- Colorado Springs --

Signed and Sealed this

Fourth Day of February, 2003

JAMES E. ROGAN
*Director of the United States Patent and Trademark Office*